United States Patent
Huang et al.

(10) Patent No.: US 12,329,521 B2
(45) Date of Patent: Jun. 17, 2025

(54) RING OF DETECTING PHYSIOLOGICAL INFORMATION

(71) Applicant: PixArt Imaging Inc., Hsin-Chu (TW)

(72) Inventors: Sen-Huang Huang, Hsin-Chu (TW); Ming Shun Manson Fei, Hsin-Chu (TW); Cong-Jun Xia, Hsin-Chu (TW)

(73) Assignee: PixArt Imaging Inc., Hsin-Chu (TW)

( * ) Notice: Subject to any disclaimer, the term of this patent is extended or adjusted under 35 U.S.C. 154(b) by 597 days.

(21) Appl. No.: 17/835,930

(22) Filed: Jun. 8, 2022

(65) Prior Publication Data
US 2022/0395201 A1 Dec. 15, 2022

(30) Foreign Application Priority Data

Jun. 11, 2021 (CN) .......................... 202110656442.1
May 5, 2022 (CN) .......................... 202210481440.8

(51) Int. Cl.
*A61B 5/1455* (2006.01)
*A44C 3/00* (2006.01)
*A61B 5/00* (2006.01)

(52) U.S. Cl.
CPC ........ *A61B 5/14552* (2013.01); *A61B 5/6802* (2013.01); *A61B 5/6826* (2013.01); *A44C 3/008* (2013.01)

(58) Field of Classification Search
CPC . A61B 5/14552; A61B 5/6802; A61B 5/6826; A61B 5/145; A44C 3/008; G06F 3/014
See application file for complete search history.

(56) References Cited

U.S. PATENT DOCUMENTS

| | | | |
|---|---|---|---|
| 2008/0171915 A1* | 7/2008 | Kawajiri | A61B 5/14551 600/300 |
| 2010/0056886 A1* | 3/2010 | Hurtubise | A61B 5/6838 600/324 |
| 2010/0168531 A1* | 7/2010 | Shaltis | A61B 5/6826 600/301 |
| 2010/0298677 A1* | 11/2010 | Lu | A61B 5/6838 600/324 |
| 2012/0238840 A1* | 9/2012 | Hashimoto | A61B 5/0075 600/310 |
| 2013/0183646 A1* | 7/2013 | Lusted | G09B 19/00 434/236 |

(Continued)

*Primary Examiner* — Michael R Bloch
*Assistant Examiner* — Abid A Mustansir
(74) *Attorney, Agent, or Firm* — Winston Hsu

(57) ABSTRACT

A ring of detecting physiological information of a user includes a case and a detection assembly. The case has an inner space including an annular region and a sunken region. The sunken region has a first lateral side, a lower bottom and a second lateral side. The first lateral side and the second lateral side are located on two sides of the sunken region and respectively connected with two sides of the annular region. The annular region covers a back of the user's finger. The lower bottom of the sunken region contacts against a finger pulp of the user's finger. The first lateral side and the second lateral side respectively contact against lateral sides of the finger. The detection assembly is disposed inside the case and includes a first detection module and a second detection module respectively located on the first lateral side and the second lateral side.

17 Claims, 4 Drawing Sheets

(56) References Cited

U.S. PATENT DOCUMENTS

| | | | |
|---|---|---|---|
| 2015/0220109 A1* | 8/2015 | Von Badinski | G06V 40/70 368/10 |
| 2016/0066845 A1* | 3/2016 | Kwon | A61B 5/6802 600/384 |
| 2019/0008396 A1* | 1/2019 | Baron | A61B 5/14552 |

* cited by examiner

RING OF DETECTING PHYSIOLOGICAL INFORMATION

BACKGROUND OF THE INVENTION

1. Field of the Invention

The present invention relates to a ring, and more particularly, to a ring of accurately detecting physiological information of the user.

2. Description of the Prior Art

A conventional physiological information sensing device is mainly disposed on the mobile phone or the watch, but the user may not be able to wear the mobile phone or the watch in some conditions; for example, when the user sleeps, the item what the user wears should be as small as possible so that the user don't feel uncomfortable. In addition to the mobile phone and the watch, a conventional wearable electronic product can provide a smart ring, and the optical sensor and the light source inside the smart ring are used to detect oxyhemoglobin. The light source alternately emits the red light and the infrared light to the user's finger, which penetrate the skin and are reflected and absorbed by the blood in the blood vessels. Absorption quantity of the red light by oxyhemoglobin is different from absorption quantity of the infrared light by the oxyhemoglobin. The optical sensor analyzes the received red light and the received infrared light to acquire an absorption ratio of the red light to the infrared light by the oxyhemoglobin for generating blood oxygen saturation. However, the ring is easily rotated on the finger, and the optical sensor cannot provide an accurate detection result of the smart ring if the optical sensor does not align with the blood vessel. Therefore, design of a smart ring of comfortably fitting on the user's finger is an important issue in the optical wearable product industry.

SUMMARY OF THE INVENTION

The present invention provides a ring of accurately detecting physiological information of the user for solving above drawbacks.

According to the claimed invention, a ring of detecting physiological information of a user includes a case and a detection assembly. The case has an inner space adapted to accommodate a finger of the user. The inner space includes an annular region and a sunken region. The sunken region has a first lateral side, a lower bottom and a second lateral side. The first lateral side and the second lateral side are located on two sides of the sunken region and respectively connected with two sides of the annular region. The annular region is adapted to cover a back of the finger. The lower bottom of the sunken region contacts against a finger pulp of the finger. The first lateral side and the second lateral side respectively contact against lateral sides of the finger. The detection assembly is disposed inside the case. The detection assembly includes a first detection module and a second detection module respectively located on the first lateral side and the second lateral side.

According to the claimed invention, the first detection module includes a first light source, and the second detection module includes a second light source and an optical receiver. The optical receiver receives a first optical penetrating signal emitted by the first light source and penetrating through the finger pulp, and further receives a second optical reflecting signal emitted by the second light source and reflected by the finger pulp.

According to the claimed invention, the first detection module includes a first optical receiver, and the second detection module includes a second optical receiver and a light source. The first optical receiver receives an optical penetrating signal emitted by the light source and penetrating through the finger pulp, and the second optical receiver receives an optical reflecting signal emitted by the light source and reflected by the finger pulp.

According to the claimed invention, the first detection module includes a first light source and a first optical receiver, and the second detection module includes a second light source and a second optical receiver. The first optical receiver receives a first optical reflecting signal emitted by the first light source and reflected by the finger pulp, and the second optical receiver receives a second optical reflecting signal emitted by the second light source and reflected by the finger pulp.

According to the claimed invention, the first detection module includes a first light source and a first optical receiver, and the second detection module includes a second light source and a second optical receiver. The first optical receiver receives a second optical penetrating signal emitted by the second light source and penetrating through the finger pulp, and the second optical receiver receives a first optical penetrating signal emitted by the first light source and penetrating through the finger pulp.

According to the claimed invention, an optical transmission path provided by the first detection module is not crossed by an optical transmission path provided by the second detection module.

According to the claimed invention, the first detection module includes a first light source, and the second detection module includes a second light source. An actuation period of the first light source is not overlapped with an actuation period of the second light source.

According to the claimed invention, the case further includes an installation chamber located between the inner space and an outer surface of the case. The ring further includes a power storage module, a power charge module and a signal transmission module disposed inside the installation chamber.

According to the claimed invention, the case further includes a first light penetrating component and a second light penetrating component. The first light penetrating component and the second light penetrating component are respectively disposed on the first lateral side and the second lateral side of the sunken region and respectively covering the first detection module and the second detection module.

According to the claimed invention, the ring further includes an induction module electrically connected to the detection assembly and disposed on an inner surface of the inner space. The induction module is adapted to induce signal change and determine whether the finger contacts the ring, so as to turn on or turn off the detection assembly accordingly.

According to the claimed invention, the physiological information is blood oxygen saturation. The first detection module and the second detection module respectively emits a plurality of optical signals in various wavelengths.

According to the claimed invention, the first detection module alternately emits the optical signals having different wavelengths, and the second detection module alternately emits the optical signals having different wavelengths.

According to the claimed invention, a maximal width of the annular region is greater than a maximal width of the sunken region.

According to the claimed invention, each of the first detection module and a second detection module belongs to one of a penetration-type detection module and a reflection-type detection module.

According to the claimed invention, the first detection module includes a first light source, and the second detection module includes a second light source. A wavelength range of the first light source is at least not partly overlapped with a wavelength range of the second light source.

According to the claimed invention, the first detection module includes a first light source adapted to switchably emit optical signals having different wavelengths.

According to the claimed invention, the second detection module includes a second light source adapted to switchably emit optical signals having different wavelengths.

The ring of the present invention can form the annular region and the sunken region inside the inner space. The finger can be covered and buckled by the annular region and the sunken region, and the finger pulp finger can be stabilized by the sunken region, so that the ring cannot be rotated relative the finger, and the detection assembly of the ring can accurately align with the lateral artery of the finger for acquiring the preferred blood oxygen saturation. The detection modules of the detection assembly can be a combination of the penetration-type detection module and the reflection-type detection module, or be the penetration-type detection module both, or be the reflection-type detection module both. The detection result of the detection assembly can be displayed on a screen of the ring, or transmitted to the external electronic device for further analysis and display.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
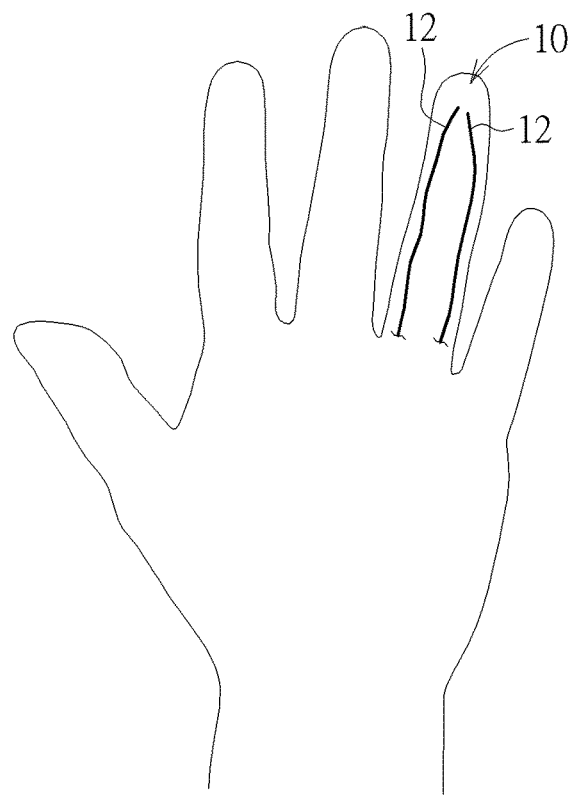
FIG. 1 is a diagram of distribution of blood vessels of a finger according to an embodiment of the present invention.
Figure 2:
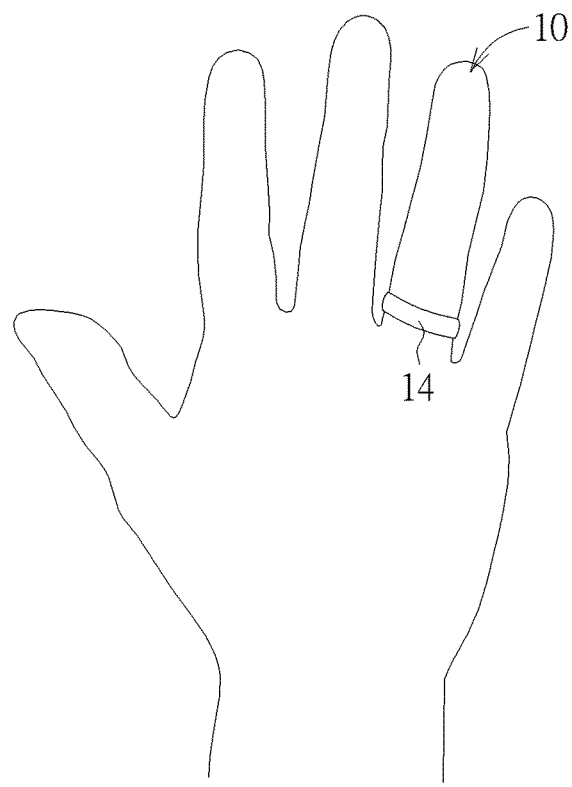
FIG. 2 is a diagram of a ring worn on the finger according to the embodiment of the present invention.

Please refer to FIG. 1 and FIG. 2. FIG. 1 is a diagram of distribution of blood vessels of a finger 10 according to an embodiment of the present invention. FIG. 2 is a diagram of a ring 14 worn on the finger 10 according to the embodiment of the present invention. As shown in FIG. 1, blood vessels 12 of the finger 10 are located on two sides of a finger pulp, which is represented as lateral artery. For detecting physiological information of a user and determining a health condition and an exercise condition of the user, absorption quantity of light with different wavelength by oxyhemoglobin can be analyzed to acquire oxygenation of hemoglobin and blood oxygen saturation of the user's artery, so that the ring 14 can detect the lateral artery (such as the blood vessel 12) of the finger 10 to acquire preferred data.

The present invention provides the smart ring 14, which can utilize optical detection technology to detect the physiological information of the user. An outward appearance of the ring 14 is similar to a conventional ring, and can be a closed circle, a C-type ring or any possible appearance. The ring 14 can have specific structural design; when the ring 14 is worn on the finger 10, the specific structural design can constrain rotation and shift of the ring 14 relative to the finger 10, so as to fix an angle of the ring 14 relative to the finger 10 and ensure that an optical detection signal emitted by the ring 14 can stably align with the blood vessel 12 of the finger 10, for acquiring the accurate blood oxygen saturation.

Figure 3:
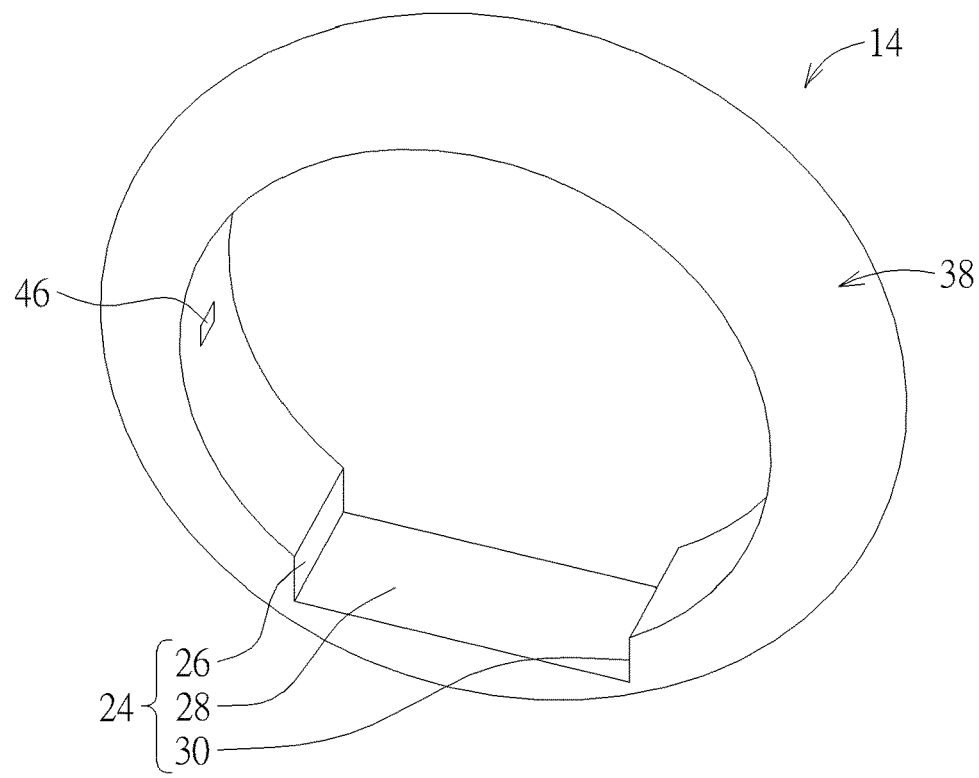
FIG. 3 is a diagram of the ring according to the embodiment of the present invention.
Figure 4:
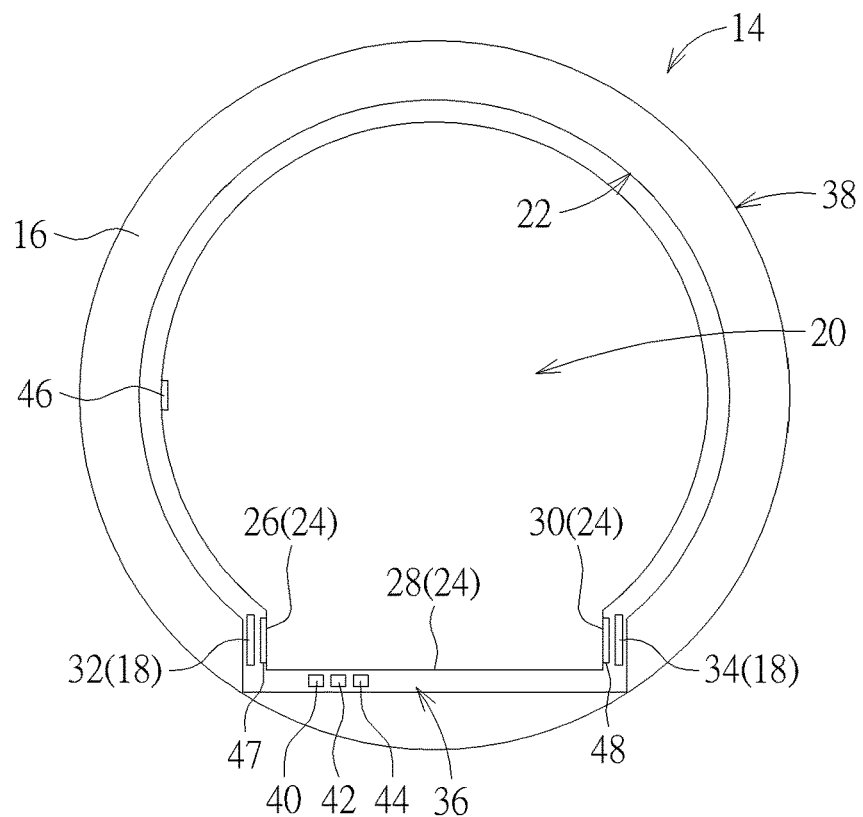
FIG. 4 is a lateral view of the ring according to the embodiment of the present invention.

Please refer to FIG. 3 and FIG. 4. FIG. 3 is a diagram of the ring 14 according to the embodiment of the present invention. FIG. 4 is a lateral view of the ring 14 according to the embodiment of the present invention. The ring 14 can include a case 16 and a detection assembly 18. The ring 14 can have an inner space 20 used to accommodate the finger 10. The inner space 20 can include an annular region 22 and a sunken region 24. The annular region 22 can cover a back of the finger 10. The sunken region 24 can contact against the finger pulp. A maximal width of the annular region 22 can be greater than a maximal width of the sunken region 24. When the ring 14 is worn on the finger 10, the finger pulp can be naturally positioned inside the sunken region 24. The sunken region 24 can further include a first lateral side 26, a lower bottom 28 and a second lateral side 30. The first lateral side 26 and the second lateral side 30 are respectively located on two sides of the lower bottom 28, and respectively connected with two opposite ends of the annular region 22. The first lateral side 26 and the second lateral side 30 can respectively contact lateral sides of the finger 10 to align with the blood vessels 12.

The detection assembly 18 can be disposed inside the case 16 via soft material (such as rubber or adhesive) or hard material (such as plastic or metal), so as to keep position of the detection assembly 18 inside the case 16. The detection assembly 18 can include a first detection module 32 and a second detection module 34 respectively located on the first lateral side 26 and the second lateral side 30. The first detection module 32 and the second detection module 34 can have an owned optical receiver and/or an owned light source. The light source of the detection assembly 18 can emit red light having a wavelength ranged between 600-750 nm, and further can emit infrared light having a wavelength ranged between 760-900 nm. Besides, the detection assembly 18 can utilize an electronic component that can absorb and transform an optical signal into an electric signal, such as an image sensor, a photodiode or a photoresistor, to be the optical receiver. The red light and the infrared light can be alternately emitted toward the finger 10. The red light and the infrared light can pierce through the skin to be reflected and absorbed by blood in the vessel. Absorption quantity of the red light by oxyhemoglobin is different from absorption quantity of the infrared light by oxyhemoglobin. The detection assembly 18 can analyze an absorption ratio of the red light to the infrared light received by the optical receiver to generate the blood oxygen saturation.

The case 16 can further include an installation chamber 36 located between the inner space 20 and an outer surface 38 of the case 16. The ring 14 can further include a power storage module 40, a power charge module 42, a signal transmission module 44 and an induction module 46 electrically connected to the detection assembly 18. The power storage module 40 can provide power to the detection assembly 18. The power charge module 42 can charge the power storage module 40 in a wire manner or in a wireless manner. The signal transmission module 44 can transmit a detection result of the detection assembly 18 to an external electronic device for recording or analysis in the wire manner or in the wireless manner. The induction module 46 can be disposed on the inner surface of the inner space 20. The induction module 46 can be a capacitive sensor or any kind of power-economized sensor. The induction module 46 can be a switch of the ring 14. When the ring 14 is worn on the finger 10, the induction module 46 can induce signal change to determine whether the finger 10 contacts the ring 10, so as to turn on or turn off the detection assembly 18 accordingly.

The power storage module 40, the power charge module 42 and the signal transmission module 44 can be disposed inside the installation chamber 36. However, if two lateral sides or an upper side of the annular region 22, which means a range between the annular region 22 and the outer surface 38, have sufficient space, the power storage module 40, the power charge module 42 and the signal transmission module 44 may be optionally disposed on the lateral sides or the upper side of the annular region 22.

The case 16 can optionally include a first light penetrating component 47 and a second light penetrating component 48 respectively disposed on the first lateral side 26 and the second lateral side 30 of the sunken region 24. The first light penetrating component 47 and the second light penetrating component 48 can cover the first detection module 32 and the second detection module 34 to allow passing of the optical signal emitted or received by the first detection module 32 and the second detection module 34. The first light penetrating component 47 and the second light penetrating component 48 can be made by any possible transparent material, or any optical component with a condensing function, such as the concave lens, the convex lens, the light pipe, the prism or the micro lenses.

Figure 5:
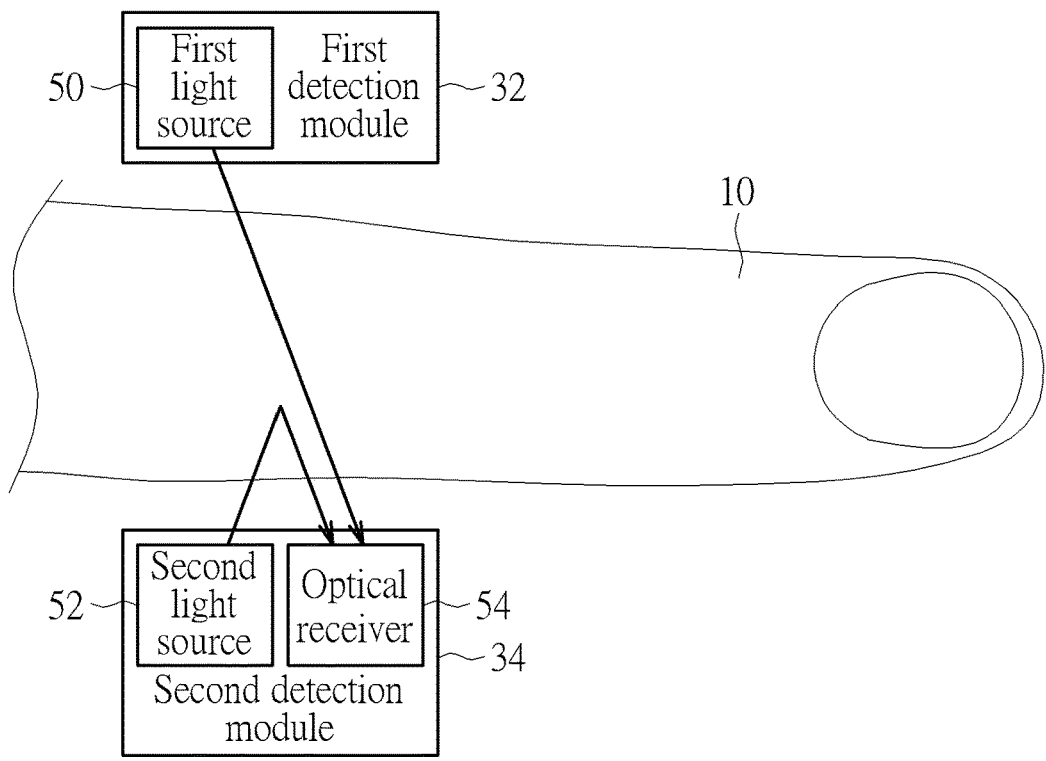
FIG. 5 is a functional block diagram of a detection assembly according to a first embodiment of the present invention.

Please refer to FIG. 5. FIG. 5 is a functional block diagram of the detection assembly 18 according to a first embodiment of the present invention. The first detection module 32 of the detection assembly 18 can include a first light source 50, and the second detection module 34 of the detection assembly 18 can include a second light source 52 and an optical receiver 54. The first light source 50 and the second light source 52 can respectively be a red light source and an infrared light source. The optical receiver 54 can receive a first optical penetrating signal (such as the red light signal and the infrared light signal) emitted by the first light source 50 and penetrating through the finger 10, and further receive a second optical reflecting signal (such as the red light signal and the infrared light signal) emitted by the second light source 52 and reflected from the finger 10.

Figure 6:
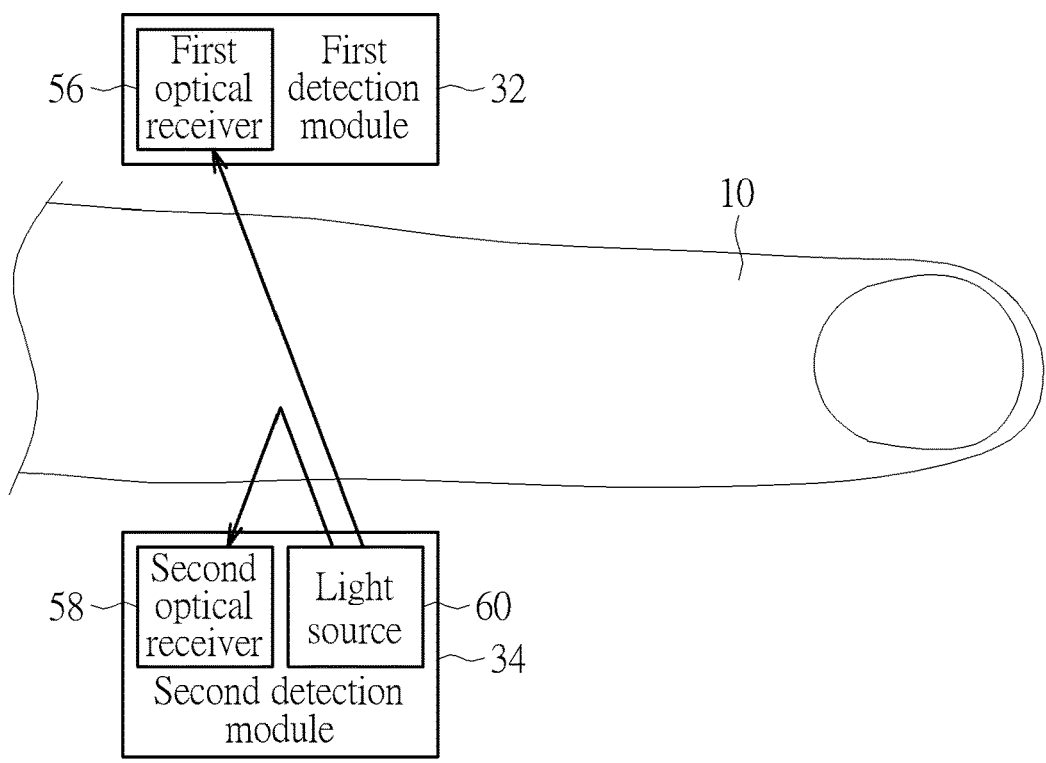
FIG. 6 is a functional block diagram of the detection assembly according to a second embodiment of the present invention.

Please refer to FIG. 6. FIG. 6 is a functional block diagram of the detection assembly 18 according to a second embodiment of the present invention. In the second embodiment, the first detection module 32 can include a first optical receiver 56, and the second detection module 34 can include a second optical receiver 58 and a light source 60. The first optical receiver 56 can receive the first optical penetrating signal (such as the red light signal and the infrared light signal) emitted by the light source 60 and penetrating through the finger 10. The second optical receiver 58 can receive the second optical reflecting signal (such as the red light signal and the infrared light signal) emitted by the light source 60 and reflected from the finger 10.

Figure 7:
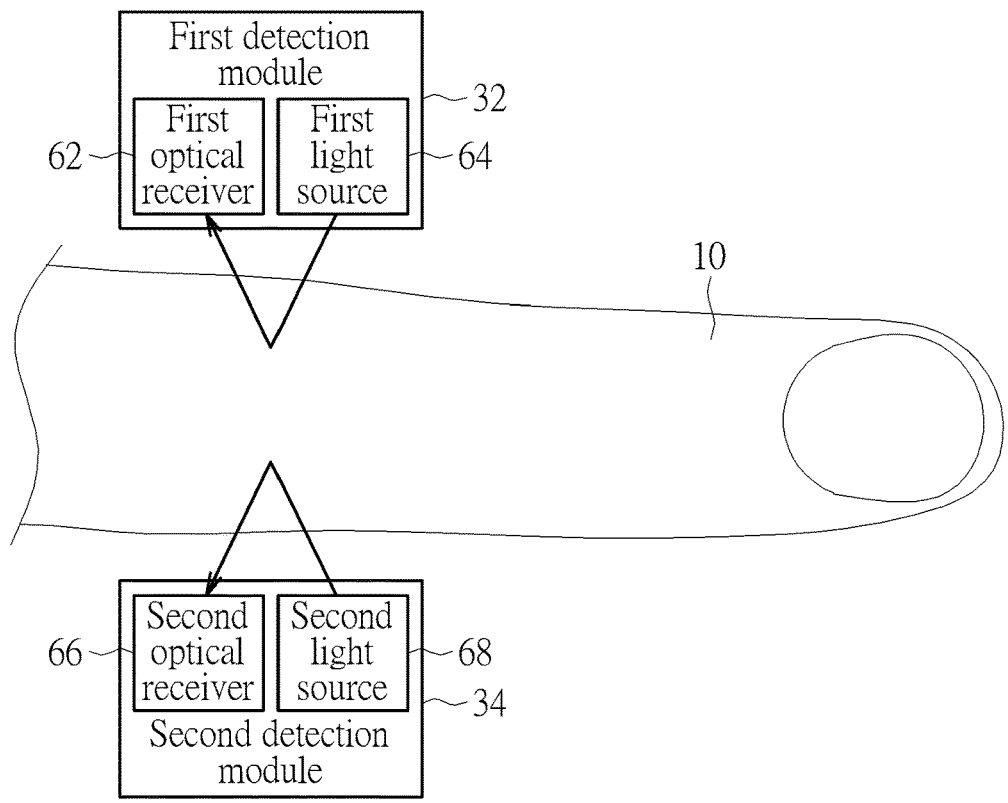
FIG. 7 is a functional block diagram of the detection assembly according to a third embodiment of the present invention.

Please refer to FIG. 7. FIG. 7 is a functional block diagram of the detection assembly 18 according to a third embodiment of the present invention. In the third embodiment, the first detection module 32 can include a first optical receiver 62 and a first light source 64, and the second detection module 34 can include a second optical receiver 66 and a second light source 68. The first optical receiver 62 can receive a first optical reflecting signal (such as the red light signal and the infrared light signal) emitted by the first light source 64 and reflected from the finger 10. The second optical receiver 66 can receive the second optical reflecting signal (such as the red light signal and the infrared light signal) emitted by the second light source 68 and reflected from the finger 10.

Figure 8:
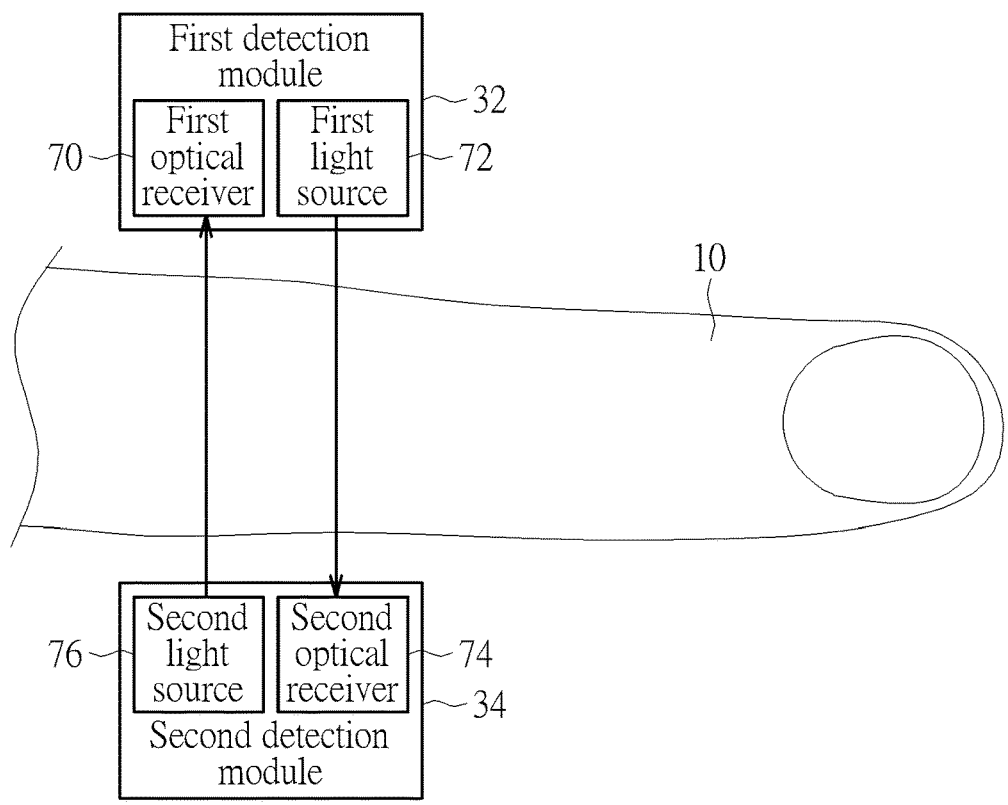
FIG. 8 is a functional block diagram of the detection assembly according to a fourth embodiment of the present invention.

Please refer to FIG. 8. FIG. 8 is a functional block diagram of the detection assembly 18 according to a fourth embodiment of the present invention. In the fourth embodiment, the first detection module 32 can include a first optical receiver 70 and a first light source 72, and the second detection module 34 can include a second optical receiver 74 and a second light source 76. The first optical receiver 70 can receive a second optical penetrating signal (such as the red light signal and the infrared light signal) emitted by the second light source 76 and penetrating through the finger 10. The second optical receiver 74 can receive the first optical penetrating signal (such as the red light signal and the infrared light signal) emitted by the first light source 72 and penetrating through the finger 10.

As the embodiments mentioned above, the ring 14 of the present invention does not constrain types of the receiver and the light source of the first detection module 32 and the second detection module 34 of the detection assembly 18, and an actual application is not limited to the four embodiments illustrated in the present invention. Any ring 14 that has the inner space 20 of the case 16 including the annular region 22 and the sunken region 24 can belong to a design scope of the present invention. The first detection module 32 and the second detection module 34 can respectively be one of a penetration-type detection module ad a reflection-type detection module, which depends on a design demand.

In the present invention, the detection assembly 18 can turn on the reflection-type detection module to execute detection of the reflection-type blood oxygen saturation; if a detection result conforms to predefined quality, the detection result of the reflection-type blood oxygen saturation can be directly used as a final detection result, or can further turn on and acquire another detection result of the penetration-type detection module to compare the detection result of the reflection-type detection module with the detection result of the penetration-type detection module. If the detection result of the reflection-type blood oxygen saturation does not conform to the predefined quality, the penetration-type detection module can be turned on and the detection result of the penetration-type blood oxygen saturation can be used as the final detection result. Moreover, the detection assembly 18 may alternately turn on the penetration-type detection module and the reflection-type detection module; for example, an actuation period of the first light source of the first detection module 32 is not overlapped with an actuation period of the second light source of the second detection module 34, or an actuation period of the receiver of the first detection module 32 is not overlapped with an actuation period of the receiver of the second detection module 34, and therefore the detection assembly 18 can analyze noise of the two detection results to decide that one of the detection results can be used as the final detection result.

It should be mentioned that the first light source of the first detection module 32 can be switched manually or automatically to emit the optical signal with different wavelengths, such as the red light having the wavelength ranged between 600-750 nm and the infrared light having the wavelength ranged between 760-900 nm. The second light source of the second detection module 34 can be switched manually or automatically to emit the optical signal with different wavelengths, and the wavelength of the optical signal emitted by the second detection module 34 can be the same as or similar to the wavelength of the optical signal emitted by the first detection module 32, or the wavelength of the optical signal emitted by the second detection module 34 can be at least not partly overlapped with the wavelength of the optical signal emitted by the first detection module 32. An optical transmission path provided by the first detection module 32 cannot be crossed by an optical transmission path provided by the second detection module 34, and the detection assembly 18 can have preferred detection quality.

In conclusion, the ring of the present invention can form the annular region and the sunken region inside the inner space. The finger can be covered and buckled by the annular region and the sunken region, and the finger pulp can be stabilized by the sunken region, so that the ring cannot be rotated relative the finger, and the detection assembly of the ring can accurately align with the lateral artery of the finger for acquiring the preferred blood oxygen saturation. The detection modules of the detection assembly can be a combination of the penetration-type detection module and the reflection-type detection module, or be the penetration-type detection module both, or be the reflection-type detection module both. The detection result of the detection assembly can be displayed on a screen (which is not shown in the figures) of the ring, or transmitted to the external electronic device for further analysis and display.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A ring of detecting physiological information of a user, the ring comprising:
    a case having an inner space adapted to accommodate a finger of the user, the inner space comprising an annular region and a sunken region, the sunken region having a first lateral side, a lower bottom and a second lateral side, the first lateral side and the second lateral side being located on two sides of the sunken region and respectively connected with two sides of the annular region, the annular region being adapted to cover a back of the finger, the lower bottom of the sunken region contacting against a finger pulp of the finger, the first lateral side and the second lateral side respectively contacting against lateral sides of the finger; and
    a detection assembly disposed inside the case, the detection assembly comprising a first detection module and a second detection module respectively located on the first lateral side and the second lateral side.

2. The ring of claim 1, wherein the first detection module comprises a first light source, the second detection module comprises a second light source and an optical receiver, the optical receiver receives a first optical penetrating signal emitted by the first light source and penetrating through the finger pulp, and further receives a second optical reflecting signal emitted by the second light source and reflected by the finger pulp.

3. The ring of claim 1, wherein the first detection module comprises a first optical receiver, the second detection module comprises a second optical receiver and a light source, the first optical receiver receives an optical penetrating signal emitted by the light source and penetrating through the finger pulp, the second optical receiver receives an optical reflecting signal emitted by the light source and reflected by the finger pulp.

4. The ring of claim 1, wherein the first detection module comprises a first light source and a first optical receiver, the second detection module comprises a second light source and a second optical receiver, the first optical receiver receives a first optical reflecting signal emitted by the first light source and reflected by the finger pulp, the second optical receiver receives a second optical reflecting signal emitted by the second light source and reflected by the finger pulp.

5. The ring of claim 1, wherein the first detection module comprises a first light source and a first optical receiver, the second detection module comprises a second light source and a second optical receiver, the first optical receiver receives a second optical penetrating signal emitted by the second light source and penetrating through the finger pulp, the second optical receiver receives a first optical penetrating signal emitted by the first light source and penetrating through the finger pulp.

6. The ring of claim 1, wherein an optical transmission path provided by the first detection module is not crossed by an optical transmission path provided by the second detection module.

7. The ring of claim 1, wherein the first detection module comprises a first light source, the second detection module comprises a second light source, an actuation period of the first light source is not overlapped with an actuation period of the second light source.

8. The ring of claim 1, wherein the case further comprises an installation chamber located between the inner space and an outer surface of the case, the ring further comprises a power storage module, a power charge module and a signal transmission module disposed inside the installation chamber.

9. The ring of claim 8, wherein the case further comprises a first light penetrating component and a second light penetrating component, the first light penetrating component and the second light penetrating component are respectively disposed on the first lateral side and the second lateral side of the sunken region and respectively covering the first detection module and the second detection module.

10. The ring of claim 1, wherein the ring further comprises an induction module electrically connected to the detection assembly and disposed on an inner surface of the inner space, the induction module is adapted to induce signal change and determine whether the finger contacts the ring, so as to turn on or turn off the detection assembly accordingly.

11. The ring of claim 1, wherein the physiological information is blood oxygen saturation, the first detection module and the second detection module respectively emits a plurality of optical signals in various wavelengths.

12. The ring of claim 11, wherein the first detection module alternately emits the optical signals having different wavelengths, the second detection module alternately emits the optical signals having different wavelengths.

13. The ring of claim 1, wherein a maximal width of the annular region is greater than a maximal width of the sunken region.

14. The ring of claim 1, wherein each of the first detection module and a second detection module belongs to one of a penetration-type detection module and a reflection-type detection module.

15. The ring of claim 1, wherein the first detection module comprises a first light source, the second detection module comprises a second light source, a wavelength range of the first light source is at least not partly overlapped with a wavelength range of the second light source.

16. The ring of claim 1, wherein the first detection module comprises a first light source adapted to switchably emit optical signals having different wavelengths.

17. The ring of claim 1, wherein the second detection module comprises a second light source adapted to switchably emit optical signals having different wavelengths.

* * * * *